United States Patent [19]
Gilbert et al.

[11] Patent Number: 5,647,872
[45] Date of Patent: Jul. 15, 1997

[54] SPINAL SUPPORT PLATES

[75] Inventors: Stephen Gilbert, Warsaw, Ind.; Donald Chow, 14 Rideau Shorte Court, Nepean, Ontario, Canada, K2C 3Y8; Robin Black, Calgary, Canada; Gordon Armstrong, Merrickville, Canada

[73] Assignee: Donald Chow, Ottawa, Canada

[21] Appl. No.: 87,751

[22] PCT Filed: Jan. 10, 1992

[86] PCT No.: PCT/CA92/00009
§ 371 Date: Apr. 19, 1995
§ 102(e) Date: Apr. 19, 1995

[87] PCT Pub. No.: WO92/11819
PCT Pub. Date: Jul. 23, 1992

[30] Foreign Application Priority Data

Jan. 14, 1991 [CA] Canada .................. 2034126

[51] Int. Cl.⁶ .................................................. A61B 17/56
[52] U.S. Cl. .................. 606/61; 606/60; 606/72; 606/69
[58] Field of Search ............... 606/60, 61, 69, 606/70, 71, 72, 73

[56] References Cited

U.S. PATENT DOCUMENTS

| | | | |
|---|---|---|---|
| 4,448,191 | 5/1984 | Rodynasky et al. | 606/61 |
| 5,084,049 | 1/1992 | Asher et al. | 606/61 |
| 5,364,399 | 11/1994 | Lowery et al. | 606/69 |
| 5,413,577 | 5/1995 | Pollock | 606/69 |
| 5,429,639 | 7/1995 | Judet | 606/61 |

FOREIGN PATENT DOCUMENTS

| | | | |
|---|---|---|---|
| 0360139 | 3/1990 | European Pat. Off. | |
| 2405061 | 5/1979 | France | |
| 3114136 | 10/1982 | Germany | 606/69 |

OTHER PUBLICATIONS

Clinical Orthopaedics and Related Research No. 277, Feb. 1988, Philadelphia pp. 135–142.

R.C. Black et al: 'A Contoured Anterior Spinal Fixation Plate' see first sentence; see figures 1–4.

*Primary Examiner*—Mark S. Leonardo

[57] ABSTRACT

A spinal plate is provided that has two components of curvature in the lower surface that opposes the spinal vertebrae. This lower surface preferably has the shape of a toroidal segment. A series of plates may be taken from a principal "s"-shaped template of similar shape on its lower surface. For convenience of manufacture, the shape of the curvature of the "S"-shaped template along the sides of the template is circular. A special hole pattern is also disclosed in respect of a tapered thoracic portion of the template.

6 Claims, 8 Drawing Sheets

SPINAL SUPPORT PLATES

FIELD OF THE INVENTION

This invention relates to support and reinforcement plates for portions of the human spine. More particularly, it relates to a new shape for such plates, and a template for providing a series of spinal support plates that are dimensioned to be applied to specific regions of the human spine, for a broad range of patients.

BACKGROUND TO THE INVENTION

Surgical treatment of a degenerative spinal condition has for some time relied upon the attachment to consecutive spinal vertebrae of stabilizing, reinforcing plates. Such bone plates have been attached to the vertebrae by means of screws that are set into the bone. The surfaces of such plates bearing against the bone have been both flat and curved about a single axis. Attempts have been made to introduce specific configurations for such plates in order that they may fit more intimately against the bones they are engaging.

For background, reference may be made to an article in CLINICAL ORTHOPAEDICS AND RELATED RESEARCH Number 227, February 1988, page 135 entitled: "A Contoured Anterior Spinal Fixation Plate".

In terms of geometry, a spinal plate should be as wide as possible in cross-section in order to span the lateral side of the vertebrae to which it is attached. It should not protrude so as to interfere with blood vessels or nerve tissue. And preferably, in its long axis it should substantially follow the natural contour of the spine so that the vertebrae being reinforced may be held approximately in their normal orientation to each other.

It has been customary to produce spinal plates that are curved about a single longitudinal axis. Examples include U.S. Pat. Nos. 1,105,105; 3,695,259; 4,454,876; 4,493,317; and 4,683,878 and the plate described in the above Clinical Orthopaedics article. This curvature tends to create two parallel line-contacts between the plate and the vertebrae to which it is fastened so long as the cross-sectional radius of the plate is less than that of the vertebral body. Subject to irregularities in the vertebrae, such line contacts, when they occur at the outside edges of the spinal plate, create a maximum span between the opposed points of engagement with the vertebrae. This tends to improve and maximize the stability of the coupling between the plate and each vertebra.

While spinal plates in the past have been bent about a single axis of curvature, no successful attempts have been made, prior to this invention, to produce spinal plates that have two simultaneous forms or components of curvature.

Care must be taken in selecting the geometry of such plates to obtain an optimal compromise between features of shape and cost of manufacture. This is particularly true in the case of spinal fixation plates where a variety of different plate shapes are to be preferred, in accordance to the specific vertebrae to which they are to be attached.

It might generally be thought that the individual variety in human spinal geometry would optimally require that plates for fixation to specific individuals, should be custom shaped for that individual. This is not practical since no convenient means presently exists for the pre-surgical extraction of precise spinal dimensions; and spinal plates, at least those made of hard metal, such as plate steel, cannot be conveniently re-shaped during surgery.

While an ideal fit for each individual is not presently obtainable, it would be desirable to identify a preferred geometry for spinal plates that will allow such plates to be mass produced for large numbers of individuals, and still be reasonably close to the optimal geometry for each individual.

The challenge of defining a standard geometry for spinal plates is further complicated by the fact that spinal plates, particularly for the thoracic region, should preferably be manufactured with two separate curvatures embodied therein. As well, for the thoracic region, such plates should also be tapered in their width. In order to facilitate manufacture, it is desirable to reduce the geometry of such plates to a minimum of criteria that may readily be converted into manufacturing operations that can be carried-out by existing production machinery. Computer-controlled machine tools, operating on the basis of such criteria, may then be used to mass manufacture such plates.

It is accordingly an object of this invention to provide for a form of spinal plate that has a lower spine-opposing face that incorporates two distinct patterns or components of curvature.

It is further an object of this invention to define a template from which thoracic and lumbar spinal fixation plates may be cut which will fit, it is believed, a substantial proportion of human patients where such plates are required.

It is a still further object of this invention to provide a criteria for the distribution of screw holes on spinal plates that is optimal for the application for which such plates are intended.

The invention in its general form will first be described, and then its implementation in terms of specific embodiments will be detailed with reference to the drawings following hereafter. These embodiments are intended as examples to demonstrate the principle of the invention, and the manner of its implementation. The invention implicit in such embodiments, will then be further described, and defined, in each of the individual claims which conclude this Specification.

SUMMARY OF THE INVENTION

According to the invention, a preformed spinal plate is provided that comprises a spine-opposing face incorporating two patterns or components of curvature. More particularly, a spinal plate having a median line is provided with a lower surface that is shaped to lie along the upper surface of a torus, with its outer longitudinal edges lying substantially symmetrically astride the upper circumferential median line of the torus whereby such longitudinal edges are located at substantially an equal distance from the upper circumferential median line of the torus. The upper, circumferential median line of a torus, as defined herein, is the line of contact between a torus and an overlying plane.

The invention also comprises any one of a series of spinal reinforcement plates taken from a portion of a principal template that defines satisfactory shapes for lateral plates that may be applied to the 10 lower thoracic vertebrae from T-3 to T-12; and the five lumbar vertebrae of the human spine, inclusive.

The invention also comprises a pattern of screw holes formed in a plate for use in the thoracic region of the spine, such plate having a spine-opposing face incorporating two components of curvature, and narrowing or tapering sides.

The principal template is characterized by a reflexive "s"-shaped curvature in its longitudinal axis, corresponding to the general shape of the human spine in profile. This curvature is preferably slightly less than that of the human spine in order that such plates may be used to slightly straighten the spine, once installed.

The template may be chosen to fit the human spine or either the left or right side. Accordingly, ensuring descriptions of the template and spinal plates are intended to govern the form of the mirror image to the shapes being described.

The median line of the principal template, being oriented in general alignment with of the overall longitudinal "axis" of the principal template, lies substantially above the upper, circumferential median line of a series of imaginary toroidal surfaces.

The principal template is geometrically divided into three portions. A first, lower curved portion of the principal template, corresponding to the lumbar region of the human spine, is formed with inner and outer sides lying along portions of two near-parallel arcs having first (outermost) and second (inner) radii of approximately equal lengths. These radii are each preferably of 13.50 and 12.71 inches in length respectively and extend respectively from a pair of first and second centers, the coordinates for the first center being 5.44;–12.1 and for the second center being (5.42;–12.31). (The Origin for such co-ordinates being defined subsequently, below).

The differences in the lengths of the radii and the locations of their centers are intended to provide for smooth transitions between respective portions of the principal template, as further described below.

The lowermost terminal end of the template, beyond the commencement of the first, lower curved portion, is preferably tapered at about 45 degrees to a rounded point, conveniently of about 0.25 inches radius. This tapered portion protects the femoral arteries from abrasion on plate corners where these vessels branch-out from the base of the spine.

The first, lower curved portion of the principal template is defined as commencing at its lower end where it joins with the above described tapered portion, and extends to a first juncture with the next portion of the template. This first juncture corresponds in location with the thoracolumbar junction of the human spine. The length of this first portion may be defined by reference to the median line that passes down its length. The span of the arc which approximates the median line for the lower portion is preferably of about 20 degrees.

The origin for the system of coordinates which follows is the edge of the template at the thoracolumbar junction, on the side of the centers for the first and second radii.

The median line for the entire principal template is approximated in each portion as the arc which passes through three point positioned at the midpoints of each portion (measured widthwise), such points being located at the two ends and at the longitudinal center point of each portion, e.g. half-way between the two ends. From the geometry already provided, the co-ordinates for the center and the radius of the arc that approximates the median line for the first portion of the principal template are: (5.41; –12.69) and r=13.58 respectively.

Such arc will hereafter be referred to as being the "median line" in the first, lower curved portion of the principal template.

A second, central curved portion of the principal template, corresponding to the lower region of the thoracic vertebrae above the thoracolumbar junction and commencing at the first juncture and extending to a second juncture, is formed with inner and outer sides lying along portions of two near-parallel inner and outer arcs having third and fourth radii. These radii are respectively preferably of 28.32 and 29.88 inches in length and have third and fourth centers respectively which lie on the opposite side of said template from the first and second centers.

The coordinates of the third center are (–0.29; 29.32). The co-ordinates of the fourth center are (–0.41; 29.87). Thus, this third displacement combined with the third and fourth radii determine the width of the plate in the second central portion of the template.

The point where the arc of the fourth radius (defining the outer side of the second portion of the principal template) meets with the second juncture is the origin for this description, in cartesian co-ordinates.

The angular span of the second central portion of the principal template is 8 degrees, from the first juncture to the second juncture where the next portion of the principal template begins as measured along the median line is preferably 8 degrees. The center point for the median line in this central portion has as co-ordinates (–0.53; 29.70) and the radius defining the median line is 29.21 inches.

A third, upper thoracic portion of the principal template, commencing at the second juncture, is formed with inner and outer sides lying along portions of two intersecting arcs having fifth and sixth radii. The lengths of the fifth and sixth radii, and the locations of the fifth and sixth centers from which they respectively extend, cause the sides of the principle template to progressively narrow, proceeding from the second juncture towards the upper end of the principal template. The corners at the upper terminal end of the template are preferably rounded to avoid the presence of damaging, protruding corners.

These fifth and sixth radii are respectively preferably 28.63 inches and 24.46 inches in length. The co-ordinates of the fifth center are (–0.78; 29.62).

The co-ordinates of the sixth center are (–9.01; 24.26).

The angular span of the third upper portion of the template along its median line is preferably about 17 degrees from the second juncture to the upper, terminal end of the principal template. The center point for the median line in this portion has co-ordinates of (–0.36; 26.82) and the arc for the median line has a radius of 26.33 inches.

Through use of the geometry employed, the principal template is provided with sides of precisely circular curvature within each of the three portions. Further a line approximating the median line in each portion has been defined which is also circular in curvature within each portion. While actual dimensions have been provided, these precise values may be varied. The principal being demonstrated is that a template for spinal plates may be defined using the basic geometry that has been described. The rationale for this geometry will now be elaborated.

The width of the first portion of the principal template is determined by the first displacement between the first and second centers and the respective lengths of the first and second radii. This width, is preferably one inch, but not exactly so. By reason of the geometric construction employed, the width varies by a few thousandths of an inch along its length as explained further below.

The width of the second portion of the principal template is determined by the third displacement between the third and fourth centers and the lengths of the third and fourth radii. The width of the second portion, is also preferably one inch but will vary as in the first portion.

The width of the third portion of the principal template is determined by the taper of the opposed sides, as proceeding from the second juncture to the upper end of the principal template. The preferred width of the upper end, suitable for plates that extend to the tenth thoracic vertebrae is 0.63 inches, based on a width of one inch at the second junction.

In the lumbar and central portions, it has been indicated that, while the template is substantially of a constant width, this width is not exactly constant. This feature arises because, for convenience of manufacture, the edges are preferably defined by circular curves. These two criteria of circular edges and constant width would be met exactly only if the respective sides are based on circular arcs that have the same center.

In such a case, the inside arc must have a smaller radius, and therefore a higher curvature.

The curve of the template reflexes at the thoracolumbar junction. The central portion of the template is also of substantially constant width with preferably circular boundaries. Where these two curved portions of the principal template meet, it is desirable to minimize the degree of discontinuity that occurs at the intersection. This would be best achieved by providing that the tangents to the respective radii be aligned or co-linear at the point of intersection.

At the point of intersection of the first and second portions of the template, i.e. at the first juncture, the inner radius of the lumbar region intersects with the outer radius of the central portion, and the outer radius of the lumbar region intersects with the inner radius of the central portion. If the sides in each respective portion were to have a common center then the inner radius in one portion, having greater curvature, would intersect with an outer radius lo in the other portion, of lesser curvature. Thus two curves of opposed and differing curvature would be meeting. It is considered desirable to minimize the differences in the degrees of curvature at such junctions in order to make the transitions between the sides at the junction more smooth and regular, e.g. more nearly symmetrical.

Higher symmetry at the junction could be achieved if the reflexing arc portions each possessed the same radii of curvature. However, an object of the design of the template is to produce spinal plates for the lumbar and central thoracic portions of the spine that are of substantially constant width. This criteria of constant width cannot be achieved exactly where both the inner and outer radii in each portion of the template are of equal lengths.

A compromise may, however, be adopted by choosing an inner radius that is shorter than the outer radius for each portion by an amount which is less than the width of the template; and by also displacing the center for the inner radius by a distance equal to the complementary length necessary to provide a template portion of the desired constant width at its end portions. Such a construction will provide a template of nearly the same width in between, with the variances in width being only on the order of a few thousandths of an inch.

Thus, by this means a criteria is provided by which the inner radii in the two intersecting template portions are "flattened out" somewhat to provide smoothness of transition at the juncture between the two portions. At the same time, the width of the template in each portion is maintained at a constant value, not only at the ends of each portion, but also at the midpoint. While not precisely exact, this provides a template of substantially constant width passing from the lower end of the lumbar portion up to the upper end of the central portion.

It is for this reason that the preferred embodiment as described has differing centers and radii for each of the defining boundary portions of the principal template.

The foregoing description defines a principal template having three portions, as viewed from a longitudinal plan view. The shape of the principal template is cross-sectional view will now be described.

The principal template is characterized in its transverse shape along its longitudinal axis by a lower spine-opposing surface shape that, within each of its portions, is defined by or shaped to lie along the upper surface of a toroidal segment. A first toroidal segment, centered at a point directly below the center of the arc that approximates the median line of the principal template in the first portion, defines the lower surface shape of the template in the first, lower lumbar portion. Second and third toroidal segments, centered on the opposite side of the principal template define the lower surface shape of the template in such second and third portions.

All of the toroidal segments lie with their principal radii (meaning the radii from the center of the torus to the center point of each circle defined by radial cross-sections taken through the torus) located in the same plane. Further the upper, circumferential median lines of each toroidal segment (being the line of contact between the torus and an overlying plane) intersect their adjacent segment at the junctures of the principal template. All toroidal segments have a common tubular diameter, preferably of two inches, and have surfaces that intersect in a relatively smooth, continuous manner, particularly along their upper circumferential median lines.

Each of the toroidal segments have a center and a principal diameter that causes the upper circumferential median line of the torus to conform as closely as possible to the median line of the principal template, as projected onto its lower surface. Thus the respective toroidal segments are centered at points that are displaced directly downwardly below the respective centers for the arcs approximating the median lines in the various portions of the principal template. The amount of downward displacement is equal to the minor radius of each torus and the principal radius for each toroidal segment corresponds to the radius for each of arcs defining portions of the median line.

While use of three toroidal segments is preferred, the second segment utilized for the central portion of the template may optionally be formed as a no toroidal extension of the third toroidal segment for making plates that do not extend over the first juncture.

Where only a minor portion, e.g., equivalent to one vertebrae, of a plate taken from the upper or lower portions of the principal template lies across one of the junctures, it is permissible to substitute a simpler shape for the toroidal segment underlying the central portion of the principal template. This substituted shape may be a straight cylindrical extension to either of the toroidal segments utilized for the upper or lower portions of the principal template.

This substitution is permissible only for minor intrusions across the first and second junctures. Otherwise the preferred shape for the torus underlying the principal template should be followed.

Individual plates may be patterned on portions of the principal template constituting sub-templates. Starting from the lower end of the principal template, and proceeding along the median line of the template, sub-templates may be selected that are of a sufficient length to extend between the vertebrae to be supported. Preferably this should be limited to between two and six vertebrae, inclusive.

The lowermost sub-template for the bottom-most lumbar vertebrae should be tapered at its lower end, as described above, to minimize the risk of interference with the femoral arteries which branch in this region. Otherwise, sub-templates may have square-cut ends with rounded corners so long as the hole pattern, as defined below, permits holes to lie in opposed pairs, on opposite sides of the median line. When the hole pattern is staggered, as where sub-templates are taken from the narrowing, upper thoracic region, then the ends of the sub-templates are preferably tapered, following the separation limits for the close-packing rules for the holes, as described below.

To attach the various plates selected from sub-15 templates to the spinal vertebrae, any conventional pattern of screw-holes may be formed in each sub-template. A preferred pattern of screw holes for a sub-template will now be described. This preferred pattern of screw holes is based on spherically counter-sunk holes of the known type, all having a standard, fixed outside diameter over the entire length of the sub-template.

Within the first and second portions the holes are distributed in triplets down the length of the sub-template. The central hole of each triplet is centered on the median line of the principal template, so long as the remaining two holes in each triplet may be placed in accordance with the next following criteria. The remaining two holes in each triplet are located with their centers symmetrically disposed on opposed sides of the median line, each as closely placed to the central hole in its own and adjacent triplet as possible, while remaining separated from any adjacent hole by a center-to-center distance of at least equal to three times the radius of the counter-sunk portion of each hole. Holes are also spaced from the sides of the principal template by a center-to-edge distance equal to at least twice the radius of the counter-sunk portion of each hole. Subject to the above requirements, the holes in triplet sets are as closely packed as possible.

Eventually, as the template narrows, these criteria cannot be met. This occurs in the preferred embodiment at the position corresponding to the juncture between the vertebrae T-10 and T-9. Thereafter, the holes are located in staggered pairs, one on each side of the median line of the principal template, spaced according to the closely packed and minimum separation criteria set-out above. That is to say the holes are separated from adjacent holes by at least three radii and from the template boundary by at least two radii.

The preferred screw hole pattern may be positioned to commence at the lower end of the template, with the closest screw-holes separated from such end by a distance equal to twice the radius of the counter-sunk portion of each hole. In successive sub-templates, the hole positions may be shifted from that in the principal template to ensure that the closest screw holes to the end of each sub-template are spaced from such end by the same distance as above.

Holes along the median line are drilled vertically through the principal template. Holes along either side of the median line are drilled along lines inclined away from the vertical and angled generally towards the center of the tubular portion of the toroidal segments, preferably at an angle of seven degrees from the vertical in the first and second portions of the principal template.

A preferred material for plates made from the principal template is 316 LVM surgical steel. With such a material a preferred thickness is 0.187 inches. Such plates are not intended to be load bearing, but will serve to stabilize vertebrae while a new load-bearing element, e.g.: bone graft or bone cement, is stabilizing in place.

The curvature of the lower surface of the template in the lower and central portions of the template is selected to be greater than that of the typical vertebrae against which the spinal plates patterned thereon are intended to lie. This provides two-spaced lines of contact between the plate and the bone of each vertebrae, and minimizes the chances of a "rocking" contact being formed. It also causes the plate to engage the vertebrae with the widest possible "stance". A radius of curvature of one inch throughout the entire principal template has been found satisfactory based on the examination of cadavers. On occasion an individual may have an irregularity in the shape of their spinal vertebrae that prevents the plate from seating itself on its outside edges. In such cases, the protruding portion of the bone should be shaved off.

In the upper portion of the template where the sides are distinctly tapered, the span between the sides of the curved lower surface of the template is narrowed. As the sides of the vertebrae bodies in the thoracic region of the spine are less curved than in the lumbar region, this decrease in span ensures that plates taken from sub-templates in this region will lie in satisfactory proximity to the bone to which they are attached.

The template as described may be used to produce plates from sub-templates for application to either the right or left side of the human spine. For the lumbar region it has been found practical to apply plates from the left side. For the thoracic region it is preferable that such plates be applied from the right side.

The foregoing summarizes the principal features of the invention. The invention may be further understood by the description of the preferred embodiments of the invention in conjunction with the drawings, which now follow.

In summarizing the invention above, and in describing the preferred embodiments below, specific terminology has been resorted to for the sake of clarity. However, the invention is not intended to be limited to the specific terms so selected, and it is to be understood that each specific term includes all technical equivalents which operate in a similar manner to accomplish a similar purpose.

DESCRIPTION OF THE PREFERRED EMBODIMENTS

Figures 1, 2, 3:
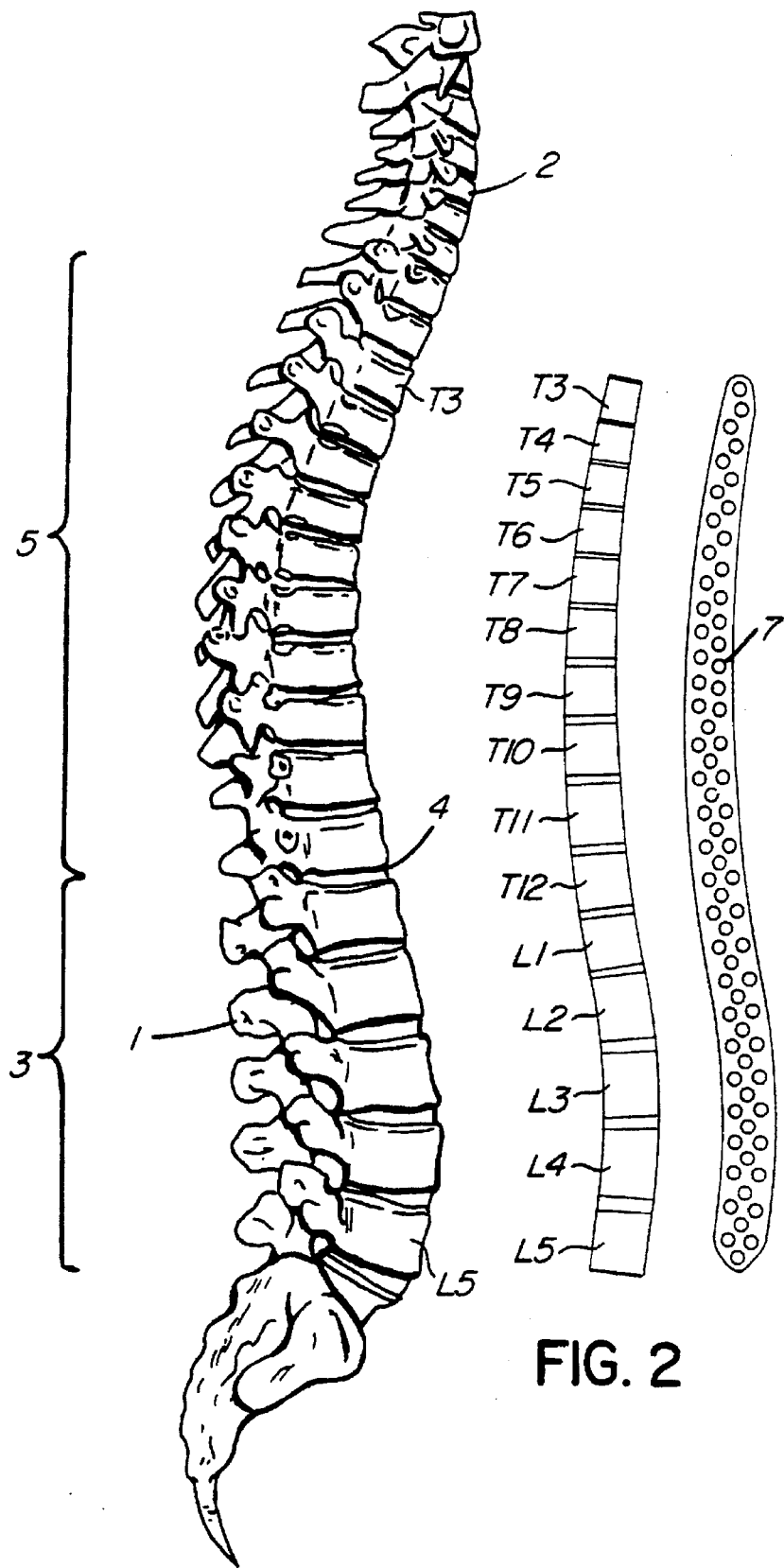
FIG. 1 is a perspective view of a human spinal column indicating the range of vertebrae over which the invention is to apply.
FIG. 2 is a schematic of spinal vertebrae from L-5 to T-3.
FIG. 3 is a plan view of the principal template of the invention, with screw-holes in place, aligned with FIGS. 2 and 1.

In FIG. 1 a spinal column 1 is shown as having vertebrae 2 in the lumbar region 3 and in the thoracic region 5. The thoracolumbar junction 4 is also identified. FIG. 2 is a schematic to indicate the numbering of the vertebrae. FIG. 3 is a plan view of the principal template 7 made in accordance with the invention, aligned with the vertebrae 2 against which it is dimensioned to fit. The principal template 7 is intended to provide a series of sub-templates for producing spinal plates 50A for use between the fifth lumbar vertebrae and third thoracic vertebrae.

Figure 4:
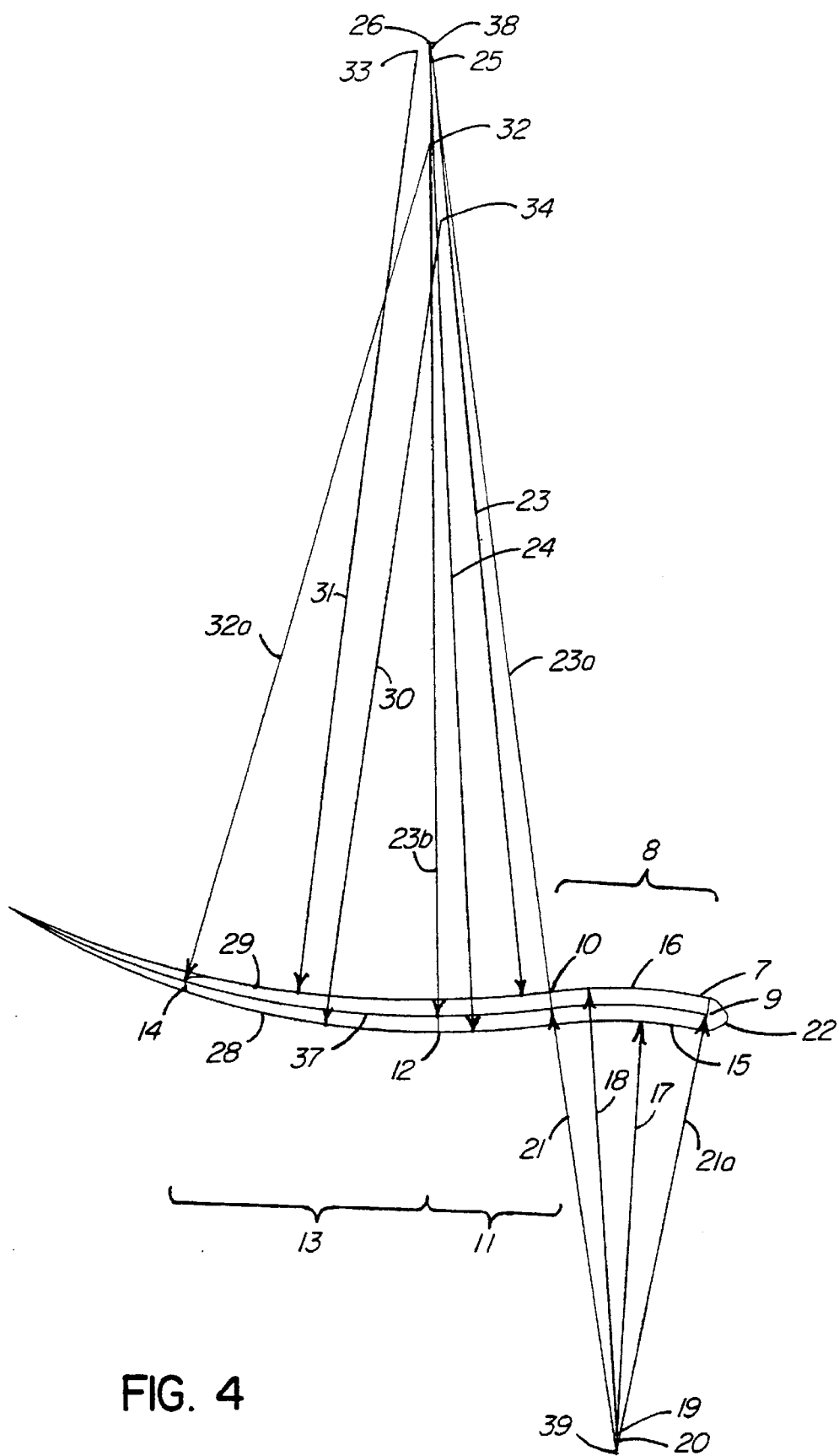
FIG. 4 is a plan view of the principal template without screw-holes in place, showing the centers for each of the principal radii.
Figure 4A:
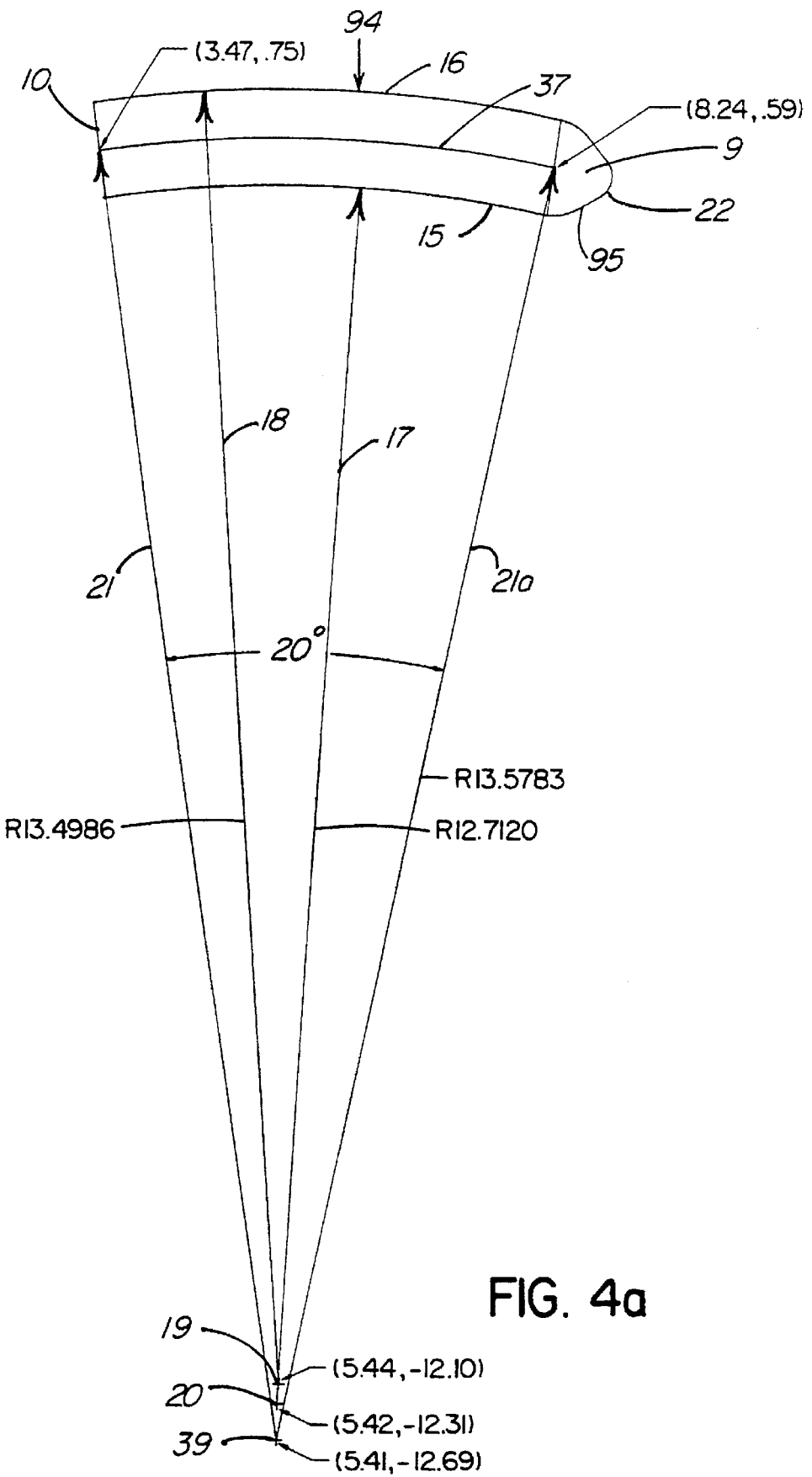
FIG. 4a is an enlarged view of the lumbar portion of FIG. 4.
Figure 4B:
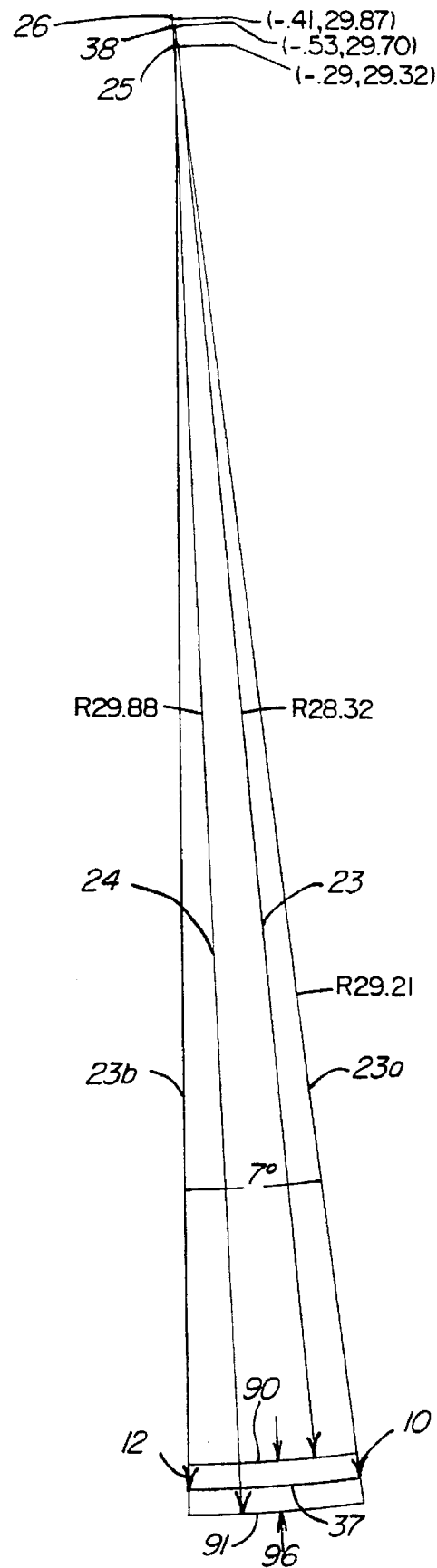
FIG. 4b is an enlarged view of the central portion of FIG. 4.
Figure 4C:
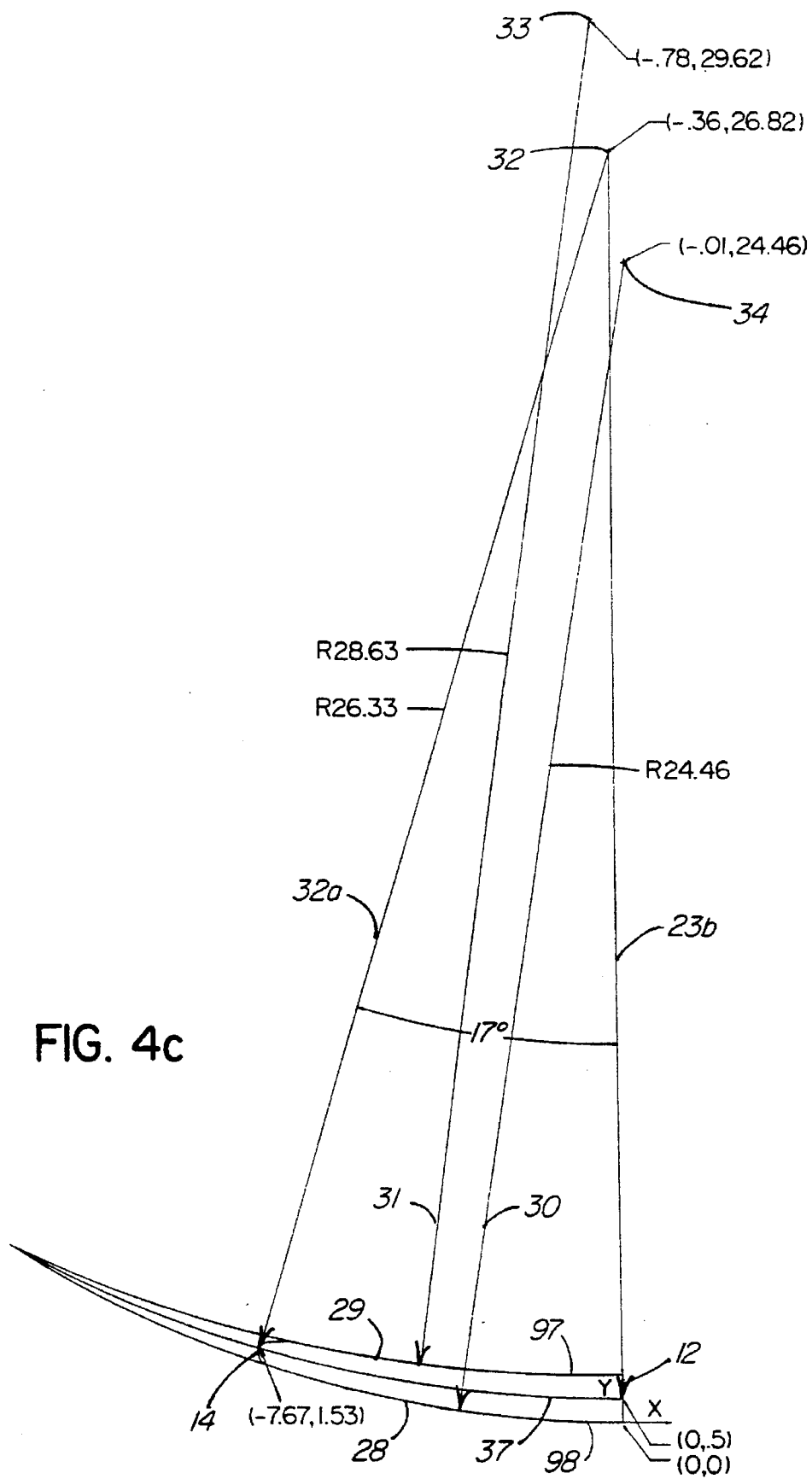
FIG. 4c is an enlarged view of the thoracic portion of FIG. 4.

In FIG. 4 the outline of the principal template 7 is shown in plan view. A first, lower, curved portion 8, shown as an enlargement in FIG. 4a, commences at the lower end 9 and extends to the first juncture 10 which forms the upper end 10 to the first portion 8. A second central portion 11, shown as an enlargement in FIG. 4b, extends to the second juncture 12. A third upper portion 13, shown as an enlargement in FIG. 4c, extends to the upper end 14.

In the first portion 8 first outer 16 and inner 15 sides are defined by arcs of first outer 18 and second inner 17 radii located at first 19 and second 20 centers on one side of the principal template. The width 94 of the template 7 is determined by the displacement between these two arcs which define the inner 15 and outer 16 sides. The length of the first, lower portion 8 is identified by the 20 degree span between the first portion bounding radius 21 extending to the median line 37 from the other first portion median center point 39 at the first juncture 10 and the first portion bounding radius 21a extending to the lower end 9.

Adopting an arbitrary origin for a cartesian system, the first center 19 is located at (5.44; −12.10) and the second center 20 is located at (5.42; −12.31). The first radius 17 is 13.50 inches in length and the second radius 18 is 12.71 inches long.

As can be seen from FIG. 4, beyond the lower end 9, the principal template 7 is formed with tapered sides 95 angled at about 45 degrees which taper to a rounded point 22 preferably having a radius of 0.25 inches.

The second central portion 11 of the principal template 7 has third, inner 23 and fourth outer 24 radii centered at third 25 and fourth 26 centers with coordinates of (−0.29; 29.32) and (−0.41; 29.87) respectively. These define the second portion inner 90 and outer 91 sides. The median line 37 of the principal template 7 is continuous through the first 10 and second 12 junctures into the third, upper portion 13 of the principal template 7. The angular span between the two second portion bounding radii 23a, 23b extending from the second portion median center point 38 for the median line in the second portion to the first junction 10, and the second juncture 12, constituting the ends of the second portion, is 8 degrees.

The inner 29 and outer 28 sides of the third upper portion 13 of the principal template 7 are defined by arcs respectively centered at a fifth center 33, having as coordinates (−0.78; 29.62) and at a sixth center 34 with coordinates (−0.01; 24.26). The third portion inner 30 and outer 31 radii defining the outer and inner boundaries 28, 29 are respectively 24.46 inches and 28.63 inches in length.

The angular span of the third upper portion 13, along its median line 37 is 17 degrees. The center 32 for this curve has coordinates of (−0.36; 26.82) and a third portion bounding radius 32a extending to the upper end 14 of the median line 37 from the second juncture of 26.33 inches.

Figure 5:
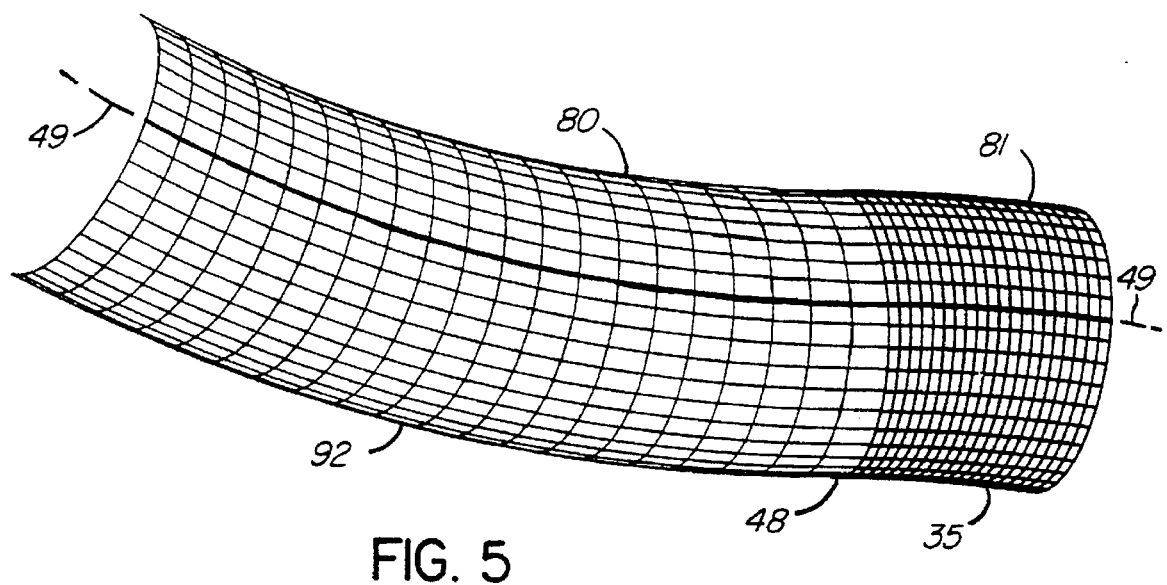
FIG. 5 is a perspective view of two intersecting toroidal segments that define a portion of the shape of the lower surface of the spinal template.

In FIG. 5 a schematic depiction of the intersection of two reflexively curved, intersecting toroidal segments 80, 81 is provided. The toruses from which they are derived have substantially the same major or minor diameters, and their principal radii lie with the same plane. A first toroidal surface segment 35 may be seen as analogous to the torus that defines the lower surface 36 of plates 40 formed from the principal template 7 in its lower portion 8. A second toroidal surface segment 92 may be seen as analogous to the torus that defines the lower surface 36 of plates 40 formed from the principal template 7 in its central portion 11. The toroidal surfaces 35, 92 preferably have identical tubular diameters of 2 inches and are continuous at their juncture 48. An upper circumferential median line 49 of the toroidal segments 80, 81 may be seen to run smoothly and continuously across the surfaces 35, 92 of both toroidal segments 80, 81. It is along this circumferential median line 49 that the median line 46 of a plate 40, corresponding to the median line 37 of the principal template 7, is aligned when forming the shape of the lower surface 36 of plates 40 taken from the principal template 7.

Figure 6:
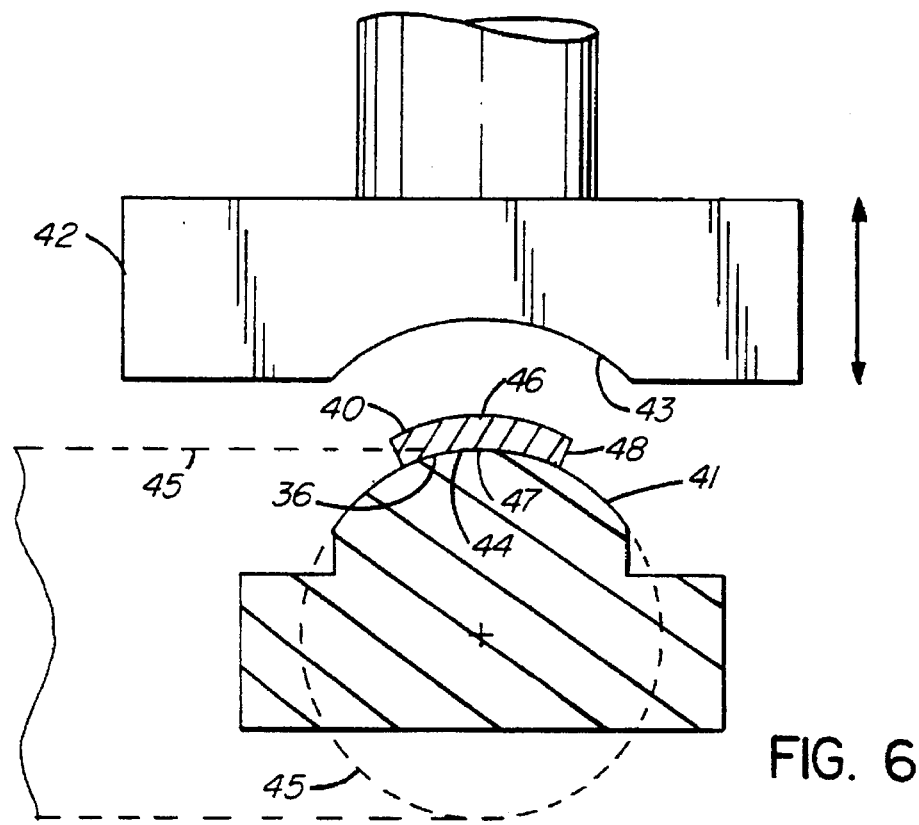
FIG. 6 is a cross-sectional view of a spinal plate shown positioned on an anvil shaped in the form of one of the toroidal segments.

This forming process is shown in FIG. 6 where a sample plate 40 having a lower surface 36 conforming to the lower surface of the principal template 7 (taken, for example, from the first portion 8) is placed on a toroidally shaped anvil 41. An upper stamping head 42 mounted in a press (not shown) has a complementary, curved forming surface 43 corresponding to that of the upper surface 44 of the anvil 41. The non-existent continuation or extension of the toroidal shape of the anvil 41 is shown in ghost outline 45.

In pressing the plate 40, the median line 46 of the plate 40, corresponding to the upper median line 37 of the principal template 7, is aligned over the upper circumferential median line 46 of the anvil surface, corresponding to the upper median circumferential line 48 of the toroidal surface segments 35, 47. In this manner, the sides 48 of the plate 40 will lie substantially symmetrically astride the upper circumferential median line 46 of the anvil 41.

To form a plate 40 that extends significantly on both sides of either the first 10 or second 12 junctures of the principal template 7, it is preferable to prepare an anvil 41 having joined upper surface segments 35, 37 analogous to those depicted in FIG. 5. However, when a plate 40 extends only slightly over one of these junctures 10, 12, it has been found satisfactory to substitute for the adjoining toroidal surface, a short straight cylindrical surface, of the same circular diameter.

Figure 9:
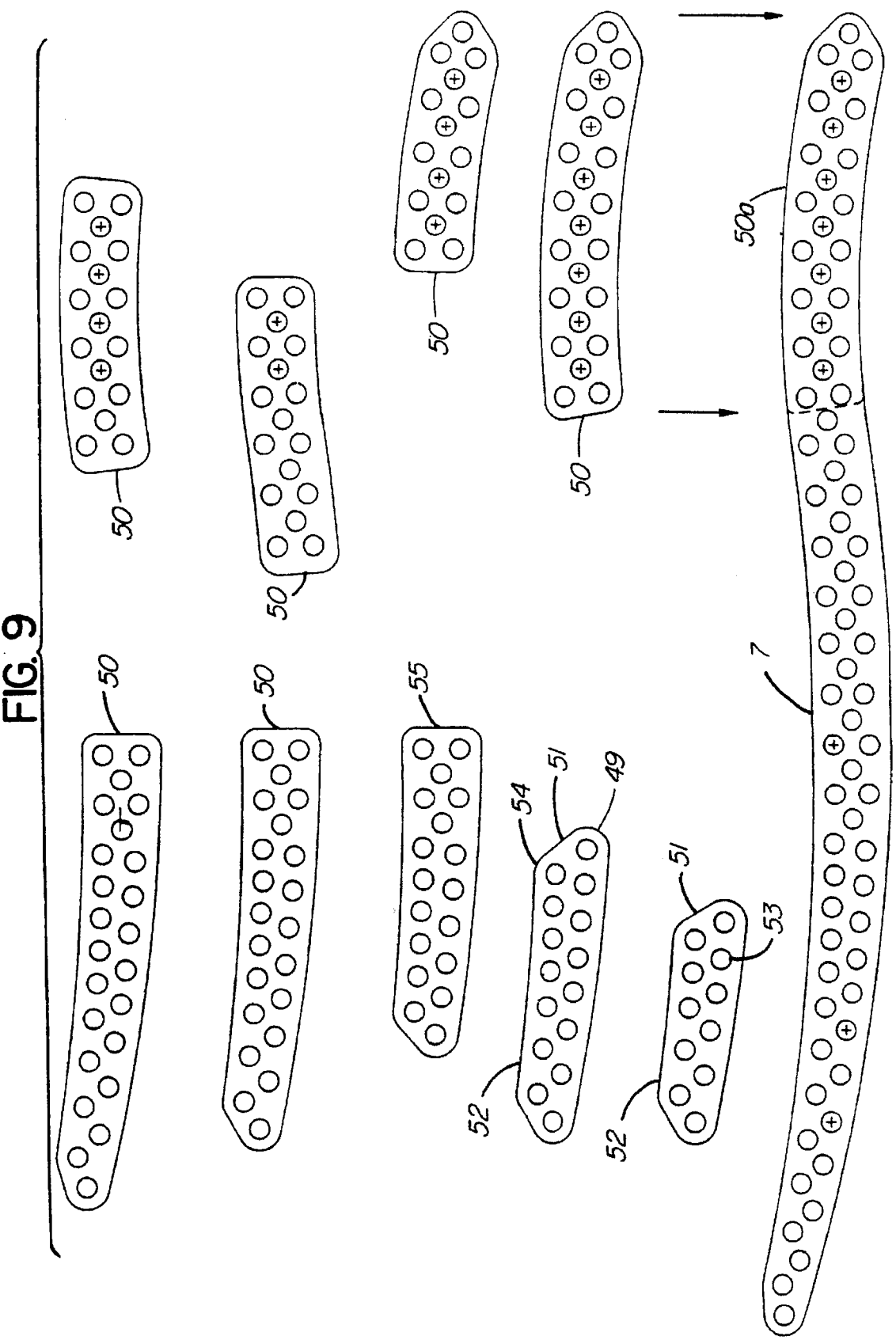
FIG. 9 is a plan view of the principal template showing a pattern of screw holes, and selected examples of sub-templates extracted therefrom.

In FIG. 9, a series of individual plates 50 are shown, corresponding to subtemplates 50A of the principal template 7.

The corners 51 on certain tapered thoracic plates 52 are shown as angled. This angling of the end 49 of such plates 52 is thought desirable to minimize the amount of plate present, consistent with the closely-packed spacing criteria preferred for the pattern of holes 53, as described further below. Where the hole pattern permits, plates 50 may have square-cut ends 55.

Figure 7:
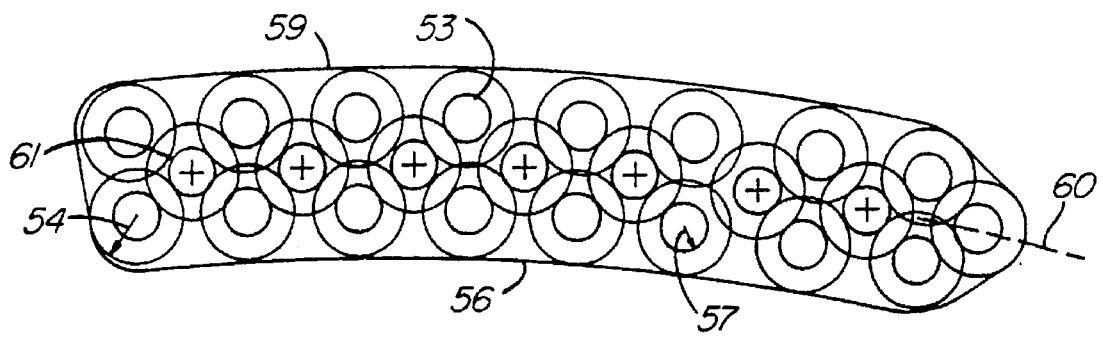
FIG. 7 is a plan view of a spinal plate taken from a sub-template for the lumbar region showing the criteria for the preferred placement of screw-holes.

In FIG. 7 the preferred hole pattern in a plate 56 which is shaped to extend to the lower-most lumbar vertebrae L-5 is shown.

The holes 53 have "forbidden zones" 54 which are defined by circles of double the radius 57 for each hole 53 including the countersunk portions (not shown). The close-packing criteria requires that such forbidden zones 54 not overlie another hole 53, nor the edges 59 of the plate 56. Otherwise, the holes 53 are distributed symmetrically about the median line 60 of the plate 56 along which centrally located holes 61 are placed, each hole 53 being as close to the central holes 61 as this close-packing criteria will permit.

Figure 7A:
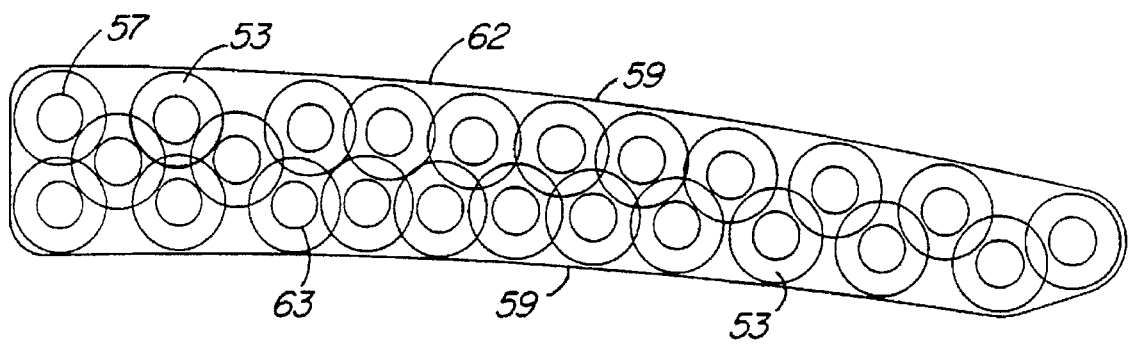
FIG. 7a is a plan view of a spinal plate taken from a sub-template for the thoracic region where the principal template narrows, showing the criteria for the preferred placement of screw-holes.

As can be seen in FIG. 9, once the template narrows sufficiently, as in sample sub-plate 62 shown in detail in FIG. 7a, the hole pattern can no longer sustain a centrally placed hole 61 and achieve maximum packing density. Thereafter, the tapered portion holes 63, should be staggered, in pairs, again as closely packed as possible without violating their forbidden zones 54.

Figure 8:
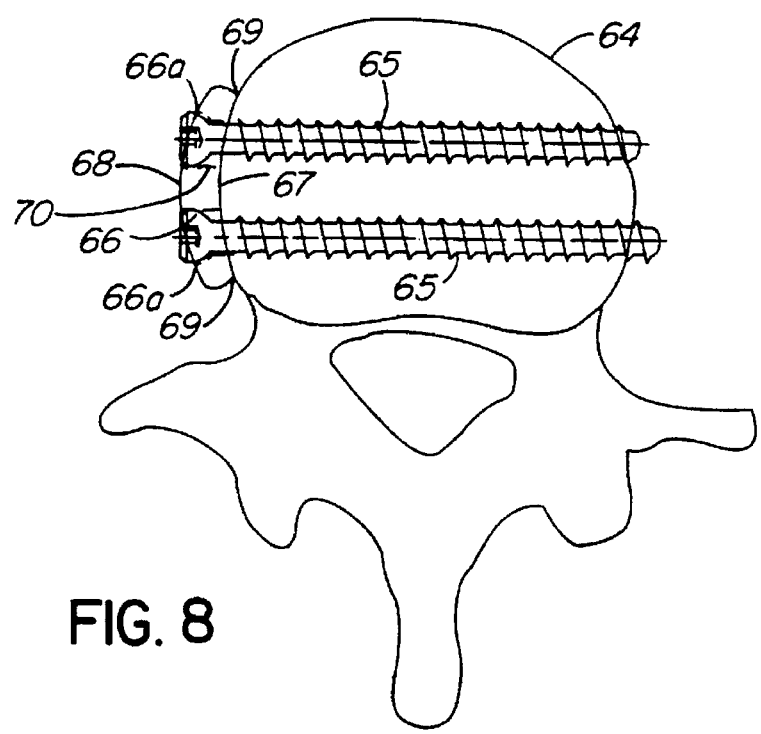
FIG. 8 is a cross-sectional view through the plate of FIG. 7 showing the alignment of the screw holes with screws engaged to a vertebrae.

The attachment format by which plates may be fastened to vertebrae is shown in FIG. 8. A vertebrae 64 is penetrated by two screws 65 having spheroidal heads 66 and seats 66a. The inner surface 67 of the plate 68 contacts the vertebrae 64 principally along the line of its outside edges 69. But ideally, when drawn-up tightly, the inner surface 67 of the plate 68 just contacts or lies slightly above the bone of the vertebrae 64. Thus the curve provided to the inner surface 67 of the plate 68 maximizes the stance and stability with which it engages the vertebrae 64.

The screws 65 preferably penetrate entirely through the vertebrae 64, being selected to be of this precise length. While the angled hole 70 below the spherical seat 66a is drilled at 7 degrees from the normal 71 to the median line 72 on the plate 68, the loose fit of the screws 65 and the spherical seat 66a allows the screws 65 to be inserted in parallel orientation. The selection of angle and length for the screws will be a matter of choice for the surgeon, according to the exigencies of the operation.

CONCLUSION

The foregoing has constituted a description of specific embodiments showing how the invention may be applied and put into use. These embodiments are only exemplary. The invention in its broadest, and more specific aspects, is further described and defined in the claims which now follow.

We claim:

1. A preformed spinal plate for fitting to a portion of the human spine, said plate comprising:
    (1) an upper surface and a spine-opposing lower surface, said surfaces being bounded by outer side surfaces extending between sand upper and lower surfaces;
    (2) said upper surface defining an imaginary median line extending longitudinally for the length of said plate and terminating at top and bottom end surfaces, said side surfaces being symmetrically disposed on either side of said median line;
    (3) said lower surface being transversely concave in curvature about said longitudinal median line; and
    (4) said side surfaces being tapered so as to progressively narrow as proceeding in the longitudinal direction defined by said median line towards said upper end surface,
wherein said median line is curved laterally with respect to said side surfaces while lying within a single plane.

2. A preformed spinal plate as in claim 1 wherein said median line is curved along an arc of a circle lying within said plane.

3. A preformed spinal plate as in claim 1 wherein said side surfaces are both curved along paths which, if extended would intersect.

4. A preformed spinal plate as in claims 1, 2 or 3 wherein said spine-opposing lower surface is shaped to lie along the upper circumferential median line of a toroidal surface segment, said upper circumferential median line being the locus of contact between the top side of a torus and a plane surface overlying such top side.

5. A preformed spinal plate as in claim 4 comprising a plurality of circular countersunk holes formed therein, said holes:
    (1) being located in staggered pairs, one on each side of said longitudinal median line, and
    (2) all having an outside diameter and corresponding radii and being distributed along the plate in a close-packed pattern whereby said holes are separated from each other by at least three hole radii and from said side surfaces by at least two hole radii.

6. A preformed spinal plate as in claim 5 wherein said holes are separated from each other by substantially three hole radii and from said side surfaces by substantially two hole radii.

* * * * *